US010403111B2

(12) United States Patent
Garg et al.

(10) Patent No.: US 10,403,111 B2
(45) Date of Patent: Sep. 3, 2019

(54) SYSTEM AND METHOD TO IDENTIFY OBSCURATION FAULT IN A FLAME DETECTOR

(71) Applicant: Honeywell International Inc., Morris Plains, NJ (US)

(72) Inventors: Amit Garg, Bangalore (IN); Raja Pratap Bommakanti, Bangalore (IN); Akshay Krishnaji Ratnaparkhe, Pune (IN); Bharat Kumar Mallela, Banglore (IN)

(73) Assignee: HONEYWELL INTERNATIONAL INC., Morris Plains, NJ (US)

( * ) Notice: Subject to any disclaimer, the term of this patent is extended or adjusted under 35 U.S.C. 154(b) by 0 days.

(21) Appl. No.: 16/033,748

(22) Filed: Jul. 12, 2018

(65) Prior Publication Data
US 2019/0019388 A1 Jan. 17, 2019

Related U.S. Application Data

(60) Provisional application No. 62/531,405, filed on Jul. 12, 2017.

(51) Int. Cl.
*G01J 5/02* (2006.01)
*G08B 17/113* (2006.01)
(Continued)

(52) U.S. Cl.
CPC .......... *G08B 17/113* (2013.01); *G01J 1/0228* (2013.01); *G01J 5/00* (2013.01);
(Continued)

(58) Field of Classification Search
CPC .......... G01J 5/0018; G01J 5/04; G01J 5/0014; G01J 5/00; G01J 5/026; G01J 5/02;
(Continued)

(56) References Cited

U.S. PATENT DOCUMENTS

| 5,812,270 A | 9/1998 | Hampton et al. |
| 6,690,460 B2 | 2/2004 | Chiu et al. |

(Continued)

FOREIGN PATENT DOCUMENTS

| DE | 4240395 A1 | 6/1994 | |
| DE | 19707418 A1 * | 8/1998 | .......... G01S 7/4812 |
| DE | 102006045916 A1 | 4/2008 | |

OTHER PUBLICATIONS

Europe Patent Application No. 18183121.5, Extended European Search Report, dated Dec. 13, 2018, 9 pages.

*Primary Examiner* — Kiho Kim
(74) *Attorney, Agent, or Firm* — Wick Phillips Gould & Martin, LLP

(57) ABSTRACT

Embodiments relate generally to systems and methods for detecting obscuration of a window of a flame detector. A flame detector may comprise a housing; a window attached to the housing, wherein the window allows radiation to pass through to the interior of the housing; a transmitter configured to emit electromagnetic radiation; a receiver configured to receive electromagnetic radiation emitted by the transmitter; and a plurality of angled surfaces configured to direct the electromagnetic radiation from the transmitter through at least a portion of the window and toward the receiver.

19 Claims, 2 Drawing Sheets

(51) Int. Cl.
  *G01J 5/00*    (2006.01)
  *G08B 17/12*   (2006.01)
  *G01J 5/08*    (2006.01)
  *G01N 21/15*   (2006.01)
  *G08B 29/04*   (2006.01)
  *G01J 1/02*    (2006.01)

(52) U.S. Cl.
  CPC ............ *G01J 5/0014* (2013.01); *G01J 5/0018*
   (2013.01); *G01J 5/02* (2013.01); *G01J 5/026*
    (2013.01); *G01J 5/0896* (2013.01); *G01N*
    *21/15* (2013.01); *G08B 17/12* (2013.01);
    *G08B 29/043* (2013.01); *G01N 2021/157*
                (2013.01)

(58) Field of Classification Search
  CPC ...... G01J 1/0228; G01J 5/0896; G08B 17/12;
    G08B 17/113; G08B 29/043; G01N
         21/15; G01N 2021/157
  See application file for complete search history.

(56) References Cited

U.S. PATENT DOCUMENTS

| | | |
|---|---|---|
| 7,948,617 B2 | 5/2011 | Shubinsky et al. |
| 7,956,329 B2 | 6/2011 | Laluvein et al. |
| 9,286,779 B2 | 3/2016 | Shaw et al. |
| 10,012,545 B2 * | 7/2018 | Lam ..................... G01J 5/0018 |
| 2009/0015824 A1 | 1/2009 | Shubkinsky et al. |
| 2010/0289650 A1 | 11/2010 | Dittmer et al. |
| 2017/0023402 A1 | 1/2017 | Follett |

* cited by examiner

SYSTEM AND METHOD TO IDENTIFY OBSCURATION FAULT IN A FLAME DETECTOR

CROSS-REFERENCE TO RELATED APPLICATIONS

The present application claims priority to U.S. Provisional Patent Application Ser. No. 62/531,405 filed Jul. 12, 2017 by Amit Garg, et al. and entitled "System and Method to Identify Obscuration Fault in a Flame Detector" which is incorporated herein by reference as if reproduced in its entirety.

STATEMENT REGARDING FEDERALLY SPONSORED RESEARCH OR DEVELOPMENT

Not applicable.

REFERENCE TO A MICROFICHE APPENDIX

Not applicable.

BACKGROUND

To prevent fires, the use of flame detectors may be incorporated into various environments, such as, for example, oil refineries, oil platforms/rigs, semiconductor fabrication plants, gas storage facilities, and/or power plants. These environments may require monitoring and an appropriate response to a fire or a potential fire situation. Flame detectors may detect a presence of a flame by sensing various spectral bands which may be emitted from the flame. Responses to a detected flame may include activating an alarm, shutting off a fuel line (e.g., a natural gas line), and/or triggering a fire suppression system.

SUMMARY

In an embodiment, a flame detector may comprise a housing; a window attached to the housing, wherein the window allows radiation to pass through to the interior of the housing; a transmitter configured to emit electromagnetic radiation; a receiver configured to receive electromagnetic radiation emitted by the transmitter; and a plurality of angled surfaces configured to direct the electromagnetic radiation from the transmitter through at least a portion of the window and toward the receiver.

In an embodiment, a detection system configured to detect obscuration of a window of a flame detector may comprise a transmitter configured to emit electromagnetic radiation; a receiver configured to receive electromagnetic radiation emitted by the transmitter; and a plurality of angled surfaces configured to direct the electromagnetic radiation from the transmitter through at least a portion of the window of the flame detector and toward the receiver.

In an embodiment, a method for detecting obscuration of a window of a flame detector may comprise emitting electromagnetic radiation from a transmitter located proximate to the window; directing the electromagnetic radiation, by a reflective surface, into a plane parallel to the plane of the window; directing the electromagnetic radiation, by a reflective surface, at least once within the plane parallel to the plane of the window; directing the electromagnetic radiation, by a reflective surface, out of the plane at least parallel to the plane of the window toward a receiver; detecting, by the receiver, the electromagnetic radiation; and determining when the detected electromagnetic radiation is below a predetermined threshold.

BRIEF DESCRIPTION OF THE DRAWINGS

For a more complete understanding of the present disclosure, reference is now made to the following brief description, taken in connection with the accompanying drawings and detailed description, wherein like reference numerals represent like parts.

DETAILED DESCRIPTION

Figure 1:
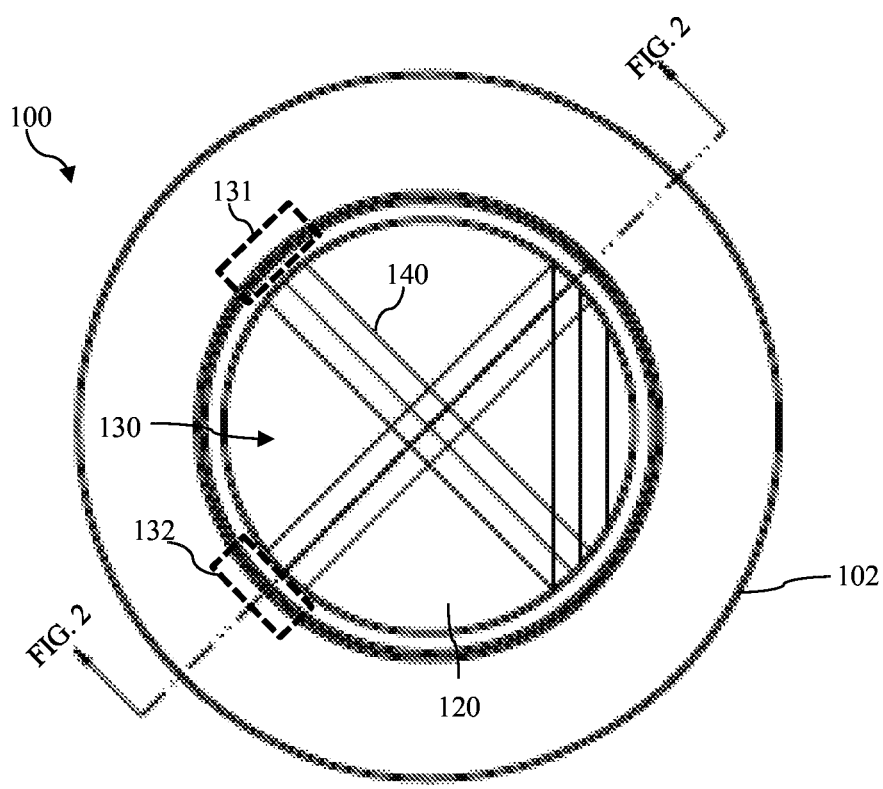
FIG. 1 illustrates a top view of a flame detector according to an embodiment of the disclosure.

It should be understood at the outset that although illustrative implementations of one or more embodiments are illustrated below, the disclosed systems and methods may be implemented using any number of techniques, whether currently known or not yet in existence. The disclosure should in no way be limited to the illustrative implementations, drawings, and techniques illustrated below, but may be modified within the scope of the appended claims along with their full scope of equivalents.

The following brief definition of terms shall apply throughout the application:

The term "comprising" means including but not limited to, and should be interpreted in the manner it is typically used in the patent context;

The phrases "in one embodiment," "according to one embodiment," and the like generally mean that the particular feature, structure, or characteristic following the phrase may be included in at least one embodiment of the present invention, and may be included in more than one embodiment of the present invention (importantly, such phrases do not necessarily refer to the same embodiment);

If the specification describes something as "exemplary" or an "example," it should be understood that refers to a non-exclusive example;

The terms "about" or "approximately" or the like, when used with a number, may mean that specific number, or alternatively, a range in proximity to the specific number, as understood by persons of skill in the art field; and If the specification states a component or feature "may," "can," "could," "should," "would," "preferably," "possibly," "typically," "optionally," "for example," "often," or "might" (or other such language) be included or have a characteristic, that particular component or feature is not required to be included or to have the characteristic. Such component or feature may be optionally included in some embodiments, or it may be excluded.

Embodiments of the disclosure include systems and methods for detecting obscuration of a window used in a flame detector. Typical flame detectors may be ultraviolet and/or infrared sensor based, and may not provide a satisfactory way to detect obscuration problems on the see-through window meant to pass electromagnetic radiation to different sensors inside the detector. The obscuration can happen due to contamination of the window by substances such as dust, fluid, water or paint. This unintended obscuration obstructs the field-of-view of a flame detector and may absorb the electromagnetic radiation before it reaches detector elements within the flame detector, which could compromise the flame detection functionality. Such conditions prevail in any outdoor space or hazardous location installation of a flame detector and impact installation in industries such as Oil and Gas Exploration and Distillery processes.

Embodiments disclose a system for determining if the window is contaminated and distinguishing a contaminated window from a clean window. The contaminants could be dust, sand, soil, mist, paint, grease, water droplets, etc. The mechanical arrangement of the system allows for reflection of a reference light source across the window, thereby scanning for obscuration of the window area covered by the light. Any contamination in that area would lead to a drop in the intensity of the light received by a light sensor, which may generate the obscuration fault.

The detection system uses reflection principles of a metallic surface. A known light source may emit electromagnetic radiation which is then reflected in such a way that it scans the window for any obstruction, and then the electromagnetic radiation is detected by a receiver. The light intensity detected by the receiver will drop if there is an obstruction in the path of the radiation. A change in the received light intensity may indicate an obstruction and may lead to the generation of an obscuration fault. The obscuration fault may comprise an alarm, alert, and/or indicator.

Referring now to FIG. 1, an exemplary flame detector 100 is shown, wherein the flame detector 100 may comprise a housing 102, a detector element 104, and a window 120 allowing radiation (such as ultraviolet and/or infrared radiation) to pass through the window 120 to the detector element 104. The detector element 104 may be configured to detect a flame based on the received radiation through the window 120.

The flame detector 100 may comprise a detection system 130 for detecting obscuration of the window 120. The detection system 130 may comprise a transmitter 131 configured to produce electromagnetic radiation 140, and a receiver 132 configured to receive the electromagnetic radiation 140. The window 120 may comprise one or more angled surfaces configured to direct the electromagnetic radiation around the window 120 and toward the receiver 132. In this regard, the angled surfaces may serve as wave guides for directing the electromagnetic radiation around the window 120 and towards the receiver 132.

Figure 2:
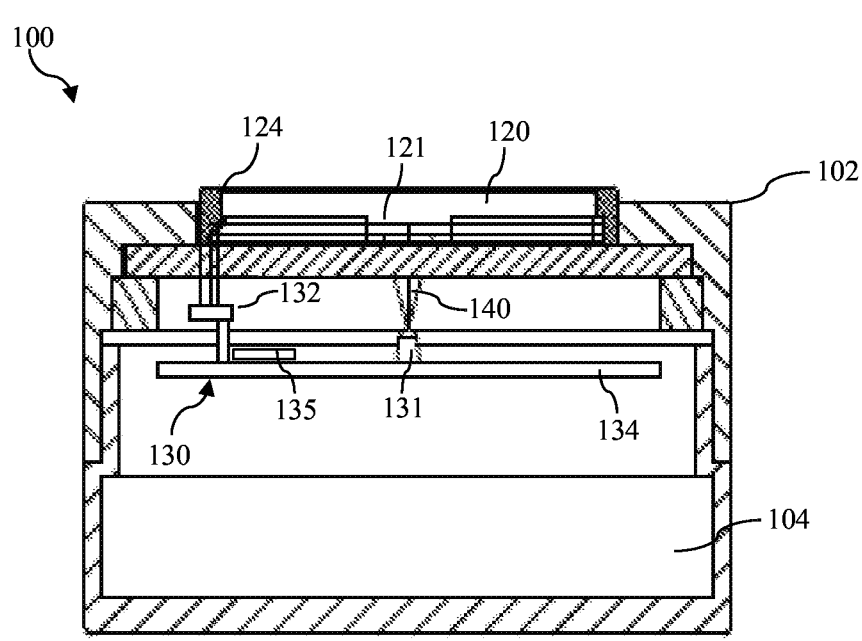
FIG. 2 illustrates a cross-sectional view of a flame detector according to an embodiment of the disclosure.

FIG. 2 illustrates a cross-sectional view of the flame detector 100, where the cross-section is illustrated in FIG. 1. The transmitter 131 and receiver 132 may be located below the plane of the window 120. The transmitter 131 may direct the electromagnetic radiation 140 toward a first angled surface 121 of the window 120. The window may comprise a plurality of angled surfaces, further described in FIGS. 3 and 4. As shown in FIG. 2, a fourth angled surface 124 may direct the electromagnetic radiation 140 toward the receiver 132. The electromagnetic radiation 140 may pass through at least a portion of the window 120. Therefore, if any of the electrometric radiation 140 is prevented from reaching the receiver 132, this may indicate that a portion of the window has been obscured by debris, damage, or another substance.

In some embodiments of the detector system 130, the transmitter 131 may continuously transmit electromagnetic radiation 140 through the window 120 (via the angled surfaces), thereby continuously monitoring the obscuration of the window 120. In some embodiments of the detector system 130, the transmitter 131 may periodically transmit electromagnetic radiation 140 through the window 120 (via the angled surfaces), thereby monitoring the obscuration of the window 120 at different times during the use-life of the window 120 and/or flame detector 100.

In some embodiments, the transmitter 131 and/or receiver 132 may be held in place within the flame detector 100 using a support 134. In some embodiments, the support 134 may comprise one or more electrical elements 135 (which may comprise communication elements) configured to control and/or communicate to/from the transmitter 131 and/or receiver 132.

Figure 3:
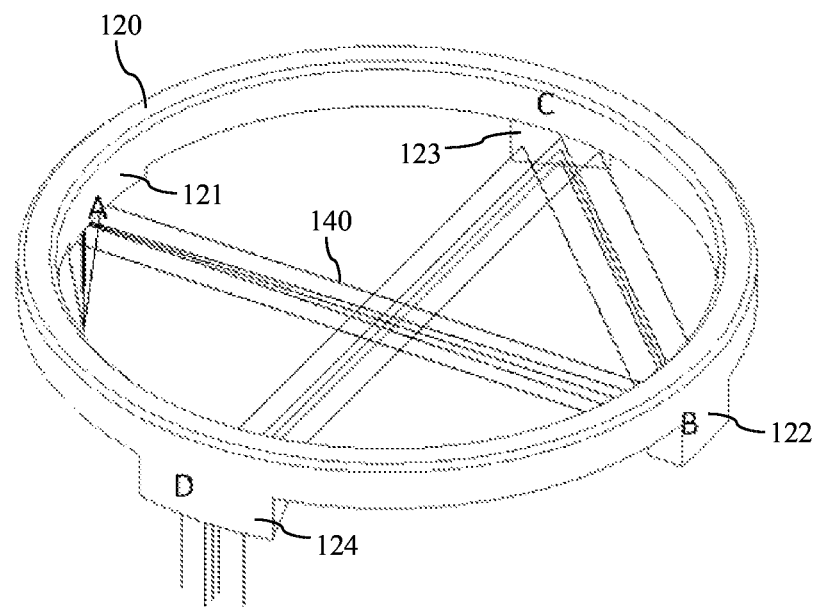
FIG. 3 illustrates a detailed view of a window for use in a flame detector according to an embodiment of the disclosure.
Figure 4:
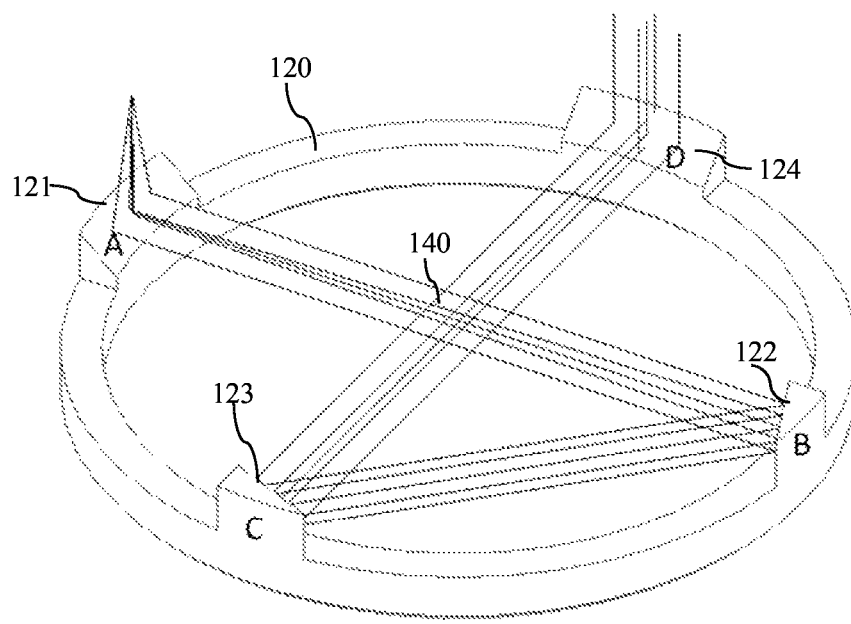
FIG. 4 illustrates another detailed view of a window for use in a flame detector according to an embodiment of the disclosure.

FIGS. 3 and 4 illustrate detailed views of the window 120 described above, wherein the window 120 may comprise one or more angled surfaces 121, 122, 123, 124 configured to direct electromagnetic radiation 140 through at least a portion of the window 120. FIG. 3 shows a top perspective view while FIG. 4 shows a bottom perspective view.

As described above, a transmitter 131 (shown in FIG. 2) may direct electromagnetic radiation 140 toward a first angled surface 121 (or Surface A). The first angled surface 121 may comprise an angle chosen to direct the electromagnetic radiation 140 through a portion of the window 120 and toward a second angled surface 122 (or Surface B). The second angled surface 122 may comprise an angle different from the angle of the first angled surface 121, in degree and/or direction. The angle of the second angled surface 122 may be chosen to direct the electromagnetic radiation 140 through a portion of the window 120 and toward a third angled surface 123 (or Surface C). The third angled surface 123 may comprise an angle different from the angle of the second angled surface 122, in degree and/or direction. The angle of the third angled surface 123 may be chosen to direct the electromagnetic radiation 140 through a portion of the window 120 and toward a fourth angled surface 124 (or Surface D). The fourth angled surface 124 may comprise an angle different from the angle of the third angled surface 123, in degree and/or direction. The angle of the fourth angled surface 124 may be chosen to direct the electromagnetic radiation 140 toward the receiver 132 (shown in FIG. 2). The use of the angled surfaces 121, 122, 123, 124 may allow the electromagnetic radiation to pass through different portions of the window 120, thereby detecting obscuration in an increased surface area of the window 120.

As shown in FIGS. 3 and 4, the first angled surface 121 may change the plane of the electromagnetic radiation 140 from the transmitter from a vertical plane (leaving the transmitter) into a horizontal plane (within the plane of the window 120). Similarly, the fourth angled surface 124 may change the plane of the electromagnetic radiation 140 from the horizontal plane (of the window 120) to a vertical plane toward the receiver. In some embodiments, the first angled surface 121 and the fourth angled surface 124 may comprise angles of similar degree and direction.

As shown in FIGS. 3 and 4, the second angled surface 122 may change the direction of the electromagnetic radiation 140 while keeping the electromagnetic radiation 140 within the horizontal plane of the window 120, directing the electromagnetic radiation 140 toward the third angled surface 123. Similarly, the third angled surface 123 may change the direction of the electromagnetic radiation 140 while keeping the electromagnetic radiation 140 within the horizontal plane of the window 120, directing the electromagnetic radiation 140 toward the fourth angled surface 124. In some embodiments, the second angled surface 122 and the third angled surface 123 may comprise angles of similar degree, but the direction of the angles may be different.

A system may comprise a housing, a viewing window in the housing surface, a source of electromagnetic radiation, a sensor with an optical filter capable of detecting the same electromagnetic radiation positioned within the housing, a multiple reflector ring placed above the window, a microprocessor for computing the signal strength, wherein the electromagnetic radiation from the source passes through the window, strikes the reflector ring, takes multiple reflections within the reflector ring and is focused back on the sensor for measuring the signal. The change in the received signal intensity will determine if there is an obstruction and lead to the generation of an obscuration fault.

The electromagnetic radiation may be reflected more than once above the window and passes twice through the window. The reflections above the window may be carried out in a plane parallel to the window surface. The coverage area above the window may be maximized with multiple reflecting tabs on the reflector. The tabs on the reflector may be at predefined angles and locations to produce the parallel beam and the coverage area. The reflecting tabs may be sized to produce the minimum required beam width and height for detecting obscuration types. The reflected signal may be measured at a sensor placed at a different location from the source. The reflected signal may be measured at the source that acts as a transceiver. The reflector may be made of the material and surface finish that is substantially reflective to the electromagnetic radiation emitted by the source. The reflector may be made of the geometry and size that fits into the housing and placed above the window. The reflecting surfaces may be made of concave or flat surfaces that can reflect and focus the beam. The window may be made of transparent material that can transmit the electromagnetic radiation in working frequency.

Having described various devices and methods herein, exemplary embodiments or aspects can include, but are not limited to:

In a first embodiment, a flame detector may comprise a housing; a window attached to the housing, wherein the window allows radiation to pass through to the interior of the housing; a transmitter configured to emit electromagnetic radiation; a receiver configured to receive electromagnetic radiation emitted by the transmitter; and a plurality of angled surfaces configured to direct the electromagnetic radiation from the transmitter through at least a portion of the window and toward the receiver.

A second embodiment can include the flame detector of the first embodiment, wherein the transmitter and the receiver are located below the plane of the window.

A third embodiment can include the flame detector of the first or second embodiments, wherein the plurality of angled surfaces comprises a first angled surface configured to direct the electromagnetic radiation from the transmitter into a plane at least parallel to the plane of the window; a second angled surface configured to direct the electromagnetic radiation within the plane at least parallel to the plane of the window; a third angled surface configured to direct the electromagnetic radiation within the plane at least parallel to the plane of the window; and a fourth angled surface configured to direct the electromagnetic radiation out of the plane at least parallel to the plane of the window toward the receiver.

A fourth embodiment can include the flame detector of any of the first through third embodiments, wherein the plurality of angled surfaces comprises at least two angled surfaces.

A fifth embodiment can include the flame detector of any of the first through fourth embodiments, wherein the plurality of angled surfaces comprises at least four angled surfaces.

A sixth embodiment can include the flame detector of any of the first through fifth embodiments, further comprising one or more electrical elements configured to process data from the receiver.

A seventh embodiment can include the flame detector of the sixth embodiment, wherein the one or more electrical element is configured to determine when the electromagnetic radiation received by the receiver is lower than a predetermined number, and to indicate an obscuration fault when the electromagnetic radiation received by the receiver is lower than the predetermined number.

An eighth embodiment can include the flame detector of any of the first through seventh embodiments, wherein the electromagnetic radiation is reflected more than once by the angled surfaces and passes at least twice through the window.

A ninth embodiment can include the flame detector of any of the first through eighth embodiments, wherein the reflections are carried out in a plane parallel to the window surface.

A tenth embodiment can include the flame detector of any of the first through ninth embodiment, wherein the plurality of angled surfaces comprises a material and surface finish that are substantially reflective to the electromagnetic radiation emitted by the transmitter.

An eleventh embodiment can include the flame detector of any of the first through tenth embodiment, wherein the transmitter and the receiver are located within the housing.

A twelfth embodiment can include the flame detector of any of the first through eleventh embodiments, wherein the plurality of angled surfaces is located within the housing.

A thirteenth embodiment can include the flame detector of any of the first through twelfth embodiments, wherein the plurality of angled surfaces is located within a plane of the window.

A fourteenth embodiment can include the flame detector of any of the first through thirteenth embodiments, wherein the plurality of angled surfaces is located above a plane of the window.

A fifteenth embodiment can include the flame detector of any of the first through fourteenth embodiments, wherein the plurality of angled surfaces is located below a plane of the window.

A sixteenth embodiment can include the flame detector of any of the first through fourteenth embodiments, wherein the plurality of angled surfaces are made of concave or flat surfaces that can reflect and focus the electromagnetic radiation.

A seventeenth embodiment can include the flame detector of any of the first through sixteenth embodiment, wherein the window is made of transparent material that can transmit the electromagnetic radiation in working frequency.

An eighteenth embodiment can include the flame detector of any of the first through seventeenth embodiments, further comprising a flame detection element configured to detect electromagnetic radiation passing through the window from the exterior of the housing to the interior of the housing, and configured to determine if a flame is detected within the field-of-view of the window.

In a nineteenth embodiment, a detection system configured to detect obscuration of a window of a flame detector may comprise a transmitter configured to emit electromagnetic radiation; a receiver configured to receive electromagnetic radiation emitted by the transmitter; and a plurality of angled surfaces configured to direct the electromagnetic radiation from the transmitter through at least a portion of the window of the flame detector and toward the receiver.

In a twentieth embodiment, a method for detecting obscuration of a window of a flame detector may comprise emitting electromagnetic radiation from a transmitter located proximate to the window; directing the electromagnetic radiation, by a reflective surface, into a plane parallel to the plane of the window; directing the electromagnetic radiation, by a reflective surface, at least once within the plane parallel to the plane of the window; directing the electromagnetic radiation, by a reflective surface, out of the plane at least parallel to the plane of the window toward a receiver; detecting, by the receiver, the electromagnetic radiation; and determining when the detected electromagnetic radiation is below a predetermined threshold.

While various embodiments in accordance with the principles disclosed herein have been shown and described above, modifications thereof may be made by one skilled in the art without departing from the spirit and the teachings of the disclosure. The embodiments described herein are representative only and are not intended to be limiting. Many variations, combinations, and modifications are possible and are within the scope of the disclosure. Alternative embodiments that result from combining, integrating, and/or omitting features of the embodiment(s) are also within the scope of the disclosure. Accordingly, the scope of protection is not limited by the description set out above, but is defined by the claims which follow that scope including all equivalents of the subject matter of the claims. Each and every claim is incorporated as further disclosure into the specification and the claims are embodiment(s) of the present invention(s). Furthermore, any advantages and features described above may relate to specific embodiments, but shall not limit the application of such issued claims to processes and structures accomplishing any or all of the above advantages or having any or all of the above features.

Additionally, the section headings used herein are provided for consistency with the suggestions under 37 C.F.R. 1.77 or to otherwise provide organizational cues. These headings shall not limit or characterize the invention(s) set out in any claims that may issue from this disclosure. Specifically and by way of example, although the headings might refer to a "Field," the claims should not be limited by the language chosen under this heading to describe the so-called field. Further, a description of a technology in the "Background" is not to be construed as an admission that certain technology is prior art to any invention(s) in this disclosure. Neither is the "Summary" to be considered as a limiting characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of the claims shall be considered on their own merits in light of this disclosure, but should not be constrained by the headings set forth herein.

Use of broader terms such as "comprises," "includes," and "having" should be understood to provide support for narrower terms such as "consisting of," "consisting essentially of," and "comprised substantially of." Use of the terms "optionally," "may," "might," "possibly," and the like with respect to any element of an embodiment means that the element is not required, or alternatively, the element is required, both alternatives being within the scope of the embodiment(s). Also, references to examples are merely provided for illustrative purposes, and are not intended to be exclusive.

While several embodiments have been provided in the present disclosure, it should be understood that the disclosed systems and methods may be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted or not implemented.

Also, techniques, systems, subsystems, and methods described and illustrated in the various embodiments as discrete or separate may be combined or integrated with other systems, modules, techniques, or methods without departing from the scope of the present disclosure. Other items shown or discussed as directly coupled or communicating with each other may be indirectly coupled or communicating through some interface, device, or intermediate component, whether electrically, mechanically, or otherwise. Other examples of changes, substitutions, and alterations are ascertainable by one skilled in the art and could be made without departing from the spirit and scope disclosed herein.

What is claimed is:

1. A flame detector comprising:
    a housing;
    a window attached to the housing, wherein the window allows radiation to pass through to the interior of the housing;
    a transmitter configured to emit electromagnetic radiation;
    a receiver configured to receive electromagnetic radiation emitted by the transmitter; and
    a plurality of angled surfaces configured to direct the electromagnetic radiation from the transmitter through at least a portion of the window and toward the receiver,
    wherein the electromagnetic radiation is reflected more than once by the plurality of angled surfaces and passes at least twice through the window.

2. The flame detector of claim 1, wherein the transmitter and the receiver are located below a plane of the window.

3. The flame detector of claim 1, wherein the plurality of angled surfaces comprises:
    a first angled surface configured to direct the electromagnetic radiation from the transmitter into a plane at least parallel to the plane of the window;
    a second angled surface configured to direct the electromagnetic radiation within the plane at least parallel to the plane of the window;
    a third angled surface configured to direct the electromagnetic radiation within the plane at least parallel to the plane of the window; and
    a fourth angled surface configured to direct the electromagnetic radiation out of the plane at least parallel to the plane of the window toward the receiver.

4. The flame detector of claim 1, wherein the plurality of angled surfaces comprises at least two angled surfaces.

5. The flame detector of claim 1, wherein the plurality of angled surfaces comprises at least four angled surfaces.

6. The flame detector of claim 1, further comprising one or more electrical elements configured to process data from the receiver.

7. The flame detector of claim 6, wherein the one or more electrical elements is configured to determine when the electromagnetic radiation received by the receiver is lower than a predetermined number, and to indicate an obscuration fault when the electromagnetic radiation received by the receiver is lower than the predetermined number.

8. The flame detector of claim 1, wherein the reflections of the electromagnetic radiation are carried out in a plane parallel to a plane of the window.

9. The flame detector of claim 1, wherein the plurality of angled surfaces comprises a material and surface finish that are substantially reflective to the electromagnetic radiation emitted by the transmitter.

10. The flame detector of claim 1, wherein the transmitter and the receiver are located within the housing.

11. The flame detector of claim 1, wherein the plurality of angled surfaces is located within the housing.

12. The flame detector of claim 1, wherein the plurality of angled surfaces is located within a plane of the window.

13. The flame detector of claim 1, wherein the plurality of angled surfaces is located above a plane of the window.

14. The flame detector of claim 1, wherein the plurality of angled surfaces is located below a plane of the window.

15. The flame detector of claim 1, wherein the plurality of angled surfaces are made of concave or flat surfaces that can reflect and focus the electromagnetic radiation.

16. The flame detector of claim 1, wherein the window is made of transparent material that can transmit the electromagnetic radiation in working frequency.

17. The flame detector of claim 1, further comprising a flame detection element configured to detect electromagnetic radiation passing through the window from the exterior of the housing to the interior of the housing, and configured to determine if a flame is detected within a field-of-view of the window.

18. A detection system configured to detect obscuration of a window of a flame detector, the detection system comprising:
   a transmitter configured to emit electromagnetic radiation;
   a receiver configured to receive electromagnetic radiation emitted by the transmitter; and
   a plurality of angled surfaces configured to direct the electromagnetic radiation from the transmitter through at least a portion of the window of the flame detector and toward the receiver,
   wherein the electromagnetic radiation is reflected more than once by the plurality of angled surfaces and passes at least twice through the window.

19. A method for detecting obscuration of a window of a flame detector, the method comprising:
   emitting electromagnetic radiation from a transmitter located proximate to the window;
   directing the electromagnetic radiation, by a first reflective surface, into a plane parallel to the plane of the window;
   directing the electromagnetic radiation, by a second reflective surface, at least once within the plane parallel to the plane of the window;
   directing the electromagnetic radiation, by a third reflective surface, out of the plane at least parallel to the plane of the window toward a receiver;
   detecting, by the receiver, the electromagnetic radiation; and
   determining when the detected electromagnetic radiation is below a predetermined threshold, wherein the electromagnetic radiation is reflected more than once and passes at least twice through the window.

* * * * *